United States Patent
Watanabe et al.

(10) Patent No.: US 6,342,364 B1
(45) Date of Patent: Jan. 29, 2002

(54) CHOLESTEROL SENSOR AND METHOD OF DETERMINING CHOLESTEROL

(75) Inventors: Motokazu Watanabe, Katano; Keiko Yugawa, Nara; Shiro Nankai, Hirakata, all of (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 09/831,091

(22) PCT Filed: Nov. 16, 2000

(86) PCT No.: PCT/JP00/08100

§ 371 Date: May 3, 2001

§ 102(e) Date: May 3, 2001

(87) PCT Pub. No.: WO01/38862

PCT Pub. Date: May 31, 2001

(30) Foreign Application Priority Data

Nov. 22, 1999 (JP) .......................................... 11-331219

(51) Int. Cl.$^7$ .............................. C12Q 1/60; C12Q 1/26
(52) U.S. Cl. ........................... 435/11; 435/25; 435/817; 435/283.1; 435/285.2; 435/287.1
(58) Field of Search ................. 435/11, 25, 817, 435/283.1, 285.2, 287.1

(56) References Cited

U.S. PATENT DOCUMENTS

| | | | |
|---|---|---|---|
| 4,185,963 A | 1/1980 | Heuck | 23/230 |
| 4,569,917 A | 2/1986 | Maier et al. | 436/71 |
| 4,746,605 A | 5/1988 | Kerscher et al. | 435/11 |
| 5,286,626 A | 2/1994 | Law et al. | 435/19 |
| 5,401,466 A | 3/1995 | Foltz et al. | 436/71 |
| 5,407,836 A | 4/1995 | Ziegenhorn et al. | 435/11 |
| 5,580,794 A | * 12/1996 | Allen | 436/169 |
| 5,814,472 A | 9/1998 | Miki et al. | 435/11 |

FOREIGN PATENT DOCUMENTS

| | | |
|---|---|---|
| EP | 764848 | 3/1997 |
| EP | 794429 | 9/1997 |
| EP | 849589 | 8/1998 |
| JP | 9-211002 | 8/1997 |
| JP | 10-38888 | 2/1998 |
| JP | 10-84997 | 4/1998 |
| JP | WO 01/38862 A1 | 5/2001 |

OTHER PUBLICATIONS

"Homogeneous Assay for Measuring Low–Density Lipoprotein Cholesterol in Serum with Triblock Copolymer and α–Cyclodextrin Sulfate", by Sugiuchi et al., Clinical Chemistry, vol. 44, No. 3 (1998), pp. 522–531.

* cited by examiner

Primary Examiner—Louise N. Leary
(74) Attorney, Agent, or Firm—McDermott, Will & Emery (57) ABSTRACT

The present invention provides a sensor that electrochemically determines cholesterol in low density lipoprotein by only one feed of a sample. The sensor has: an electrode system that is mounted on an electrically insulating base plate and includes at least a working electrode and a counter electrode; an enzyme layer formed on the base plate with the electrode system; and a reagent layer that is arranged before the enzyme layer in a sample solution supply path to the electrode system. The enzyme layer includes at least an oxidoreductase and an electron mediator. The reagent layer includes a reagent that depresses reactivity of cholesterol in lipoproteins other than the low density lipoprotein with the oxidoreductase, for example, a reagent that attaches to lipoproteins other than the low density lipoprotein to form a water-soluble complex.

8 Claims, 4 Drawing Sheets

CHOLESTEROL SENSOR AND METHOD OF DETERMINING CHOLESTEROL

TECHNICAL FIELD

The present invention relates to a sensor and a method of determining cholesterol included in low density lipoprotein in a sample like blood, serum, or plasma.

BACKGROUND ART

The concentration of cholesterol in low density lipoprotein has been noted as an important parameter in diagnosis of hypercholesterolemia.

The prior art method determines cholesterol in the low density lipoprotein by differential ultracentrifugation. This method, however, requires special equipment and disadvantageously takes a long time for measurement.

A typical method of determination without using the ultracentrifugation respectively measures the total concentration of cholesterol in a sample, the concentration of cholesterol in high density lipoprotein, and the concentration of triglyceride and calculates the concentration of cholesterol in the low density lipoprotein according to the Friedewald's equation. In the case where the sample contains a high concentration of triglyceride, however, this method has rather low degrees of confidence in reproducibility and accuracy.

Some methods of determining cholesterol in the low density lipoprotein regardless of the concentration of triglyceride have also been proposed.

The first proposed method oxidizes only cholesterol in the low density lipoprotein with an enzyme in the presence of a-cyclodextrin sulfate, dextran sulfate, magnesium ion, and polyoxyethylene-polyoxypropylene block copolyether and determines the concentration of cholesterol in the low density lipoprotein based on the degree of color development of a coloring matter (see Clinical Chemistry, Vol. 44, p522 (1998)). This method uses α-cyclodextrin sulfate, dextran sulfate, and magnesium ion to reduce the reactivity of the enzyme with cholesterol in chylomicron and cholesterol in the low density lipoprotein included in the sample, while using polyoxyethylene-polyoxypropylene block copolyether to reduce the reactivity of the enzyme with cholesterol in the high density lipoprotein in the sample.

The second proposed method oxidizes only cholesterol in the low density lipoprotein with an enzyme in the presence of an amphoteric surface active agent and aliphatic amines having either of carboxyl group and sulfonate group and determines the concentration of cholesterol in the low density lipoprotein based on the degree of color development of a coloring matter (see Japanese Laid-Open Patent Publication No. Hei 10-84997). This method reduces the reactivity of the enzyme with cholesterol included in lipoproteins other than the low-density lipoprotein in the presence of the amphoteric surface active agent.

The third proposed method treats the sample with polycation to oxidize only cholesterol in the low density lipoprotein with an enzyme and determines the concentration of cholesterol in the low density lipoprotein based on the degree of color development of a coloring matter (see U.S. Pat. No. 4,185,963).

The fourth proposed method uses porous silica to adsorb the high density lipoprotein, and causes polyanion/divalent cation to be bonded to the chylomicron and the low density lipoprotein and form an insoluble complex. The method then removes the complex as a precipitate from the solution, oxidizes only cholesterol in the low density lipoprotein with an enzyme, and determines the concentration of cholesterol in the low density lipoprotein based on the degree of color development of a coloring matter (see U.S. Pat. No. 5,401,466).

Any of the first through the fourth proposed methods discussed above enables cholesterol in the low density lipoprotein to be determined with high reproducibility and high accuracy, even in a sample having a high concentration of triglyceride.

All the first through the fourth methods determine the concentration of cholesterol based on the degree of color development of the coloring matter. These methods are thus not applicable for determination of cholesterol in originally colored samples like blood samples. For the determination of high reproducibility and high accuracy, the required process separately provides an enzyme-free first reagent and an enzyme-containing second reagent, adds only the first reagent to the sample first, and waits for addition of the second reagent until the reaction sufficiently proceeds. The procedures are accordingly rather complicated and troublesome.

DISCLOSURE OF INVENTION

The object of the present invention is thus to eliminate the above drawbacks and thus to provide a sensor that is applicable for measurement in blood sample and enables cholesterol in low density lipoprotein to be determined with high reproducibility and high accuracy by only one feed of a sample without requiring to separately add two or more reagents to the sample at different timings.

The object of the present invention is also to provide a method of determining cholesterol in the low density lipoprotein.

The present invention is directed to a cholesterol sensor for determining cholesterol in low density lipoprotein. The cholesterol sensor comprises: an electrically insulating base plate; an electrode system that is mounted on the base plate and includes at least a working electrode and a counter electrode; an enzyme layer formed on the base plate with the electrode system; and a reagent layer that is arranged before the enzyme layer in a sample solution supply path to the electrode system. The enzyme layer includes at least an oxidoreductase and an electron mediator. The reagent layer includes a reagent that attaches to lipoproteins other than the low density lipoprotein to form a water-soluble complex.

The present invention also provides a cholesterol sensor comprising: an electrically insulating base plate; an electrode system that is mounted on the base plate and includes at least a working electrode and a counter electrode; an enzyme layer formed on the base plate with the electrode system; a filter that is arranged before the enzyme layer in a sample solution supply path to the electrode system; and a reagent layer that is either carried on the filter or arranged before the filter in the sample solution supply path. The enzyme layer includes at least an oxidoreductase and an electron mediator. The reagent layer includes a reagent that functions to adsorb and/or agglutinate lipoproteins other than the low density lipoprotein.

The present invention further provides a method of determining cholesterol in low density lipoprotein. The method includes the steps of:

(a) causing a sample to react with any reagent or reagent group selected from the group consisting of (i), (ii), and (iii) specified below:
  (i) α-cyclodextrin sulfate, dextran sulfate, magnesium ion, and polyoxyethylene-polyoxypropylene block copolyether, (ii) an amphoteric surface active agent and aliphatic amines having either of carboxyl group and sulfonate group, and (iii) polycation;

(b) subsequently causing the sample to react with an oxidoreductase, which specifically reacts with cholesterol, and an electron mediator; and (c) electrochemically oxidizing the electron mediator, which has been reduced in the step (b), so as to measure a value of oxidation current.

The present invention is also directed to a method of determining cholesterol in low density lipoprotein. The method includes the steps of:

(a) causing a sample to react with polyanion, divalent cation, and either an antibody against high density lipoprotein or silica;

(b) subsequently causing the sample to react with an oxidoreductase, which specifically reacts with cholesterol, and an electron mediator; and (c) electrochemically oxidizing the electron mediator, which has been reduced in the step (b), so as to measure a value of oxidation current.

BEST MODE FOR CARRYING OUT THE INVENTION

The method of the present invention that determines cholesterol in low density lipoprotein has the steps of:

(a) causing a sample to react with one or plural specific reagents;

(b) subsequently causing the sample to react with an oxidoreductase, which specifically reacts with cholesterol, and an electron mediator; and (c) electrochemically oxidizing the electron mediator, which has been reduced in the step (b), so as to measure a value of oxidation current and determine cholesterol based on the value of oxidation current.

The step (a) is discussed first. The step (a) causes lipoproteins other than low density lipoprotein included in a sample to react with one or plural specific reagents, so as to depress the reaction of the enzyme with cholesterol in the lipoproteins other than the low density lipoprotein. Here the sample may include high density lipoprotein, low density lipoprotein, very low density lipoprotein, and chylomicron, and may be, for example, blood, serum, or plasma.

The present invention applies not the absorbance but the electrochemical technique for the determination of cholesterol and thus enables cholesterol in the low density lipoprotein to be determined even in colored blood samples and turbid serum and plasma samples.

The step (a) is actualized by either of the steps of:
(a-1) causing specific reagent or reagents to attach to lipoproteins other than the low density lipoprotein included in the sample to form a water-soluble complex, so as to reduce the reactivity of the enzyme with cholesterol in the lipoproteins other than the low density lipoprotein; and (a-2) causing the lipoproteins other than the low density lipoprotein included in the sample to be adsorbed and/or agglutinated by specific reagents.

The step (a-1) is discussed in detail.

The step (a-1) uses any reagent or reagent group selected from the group consisting of (i), (ii), and (iii) specified below:

(i) α-cyclodextrin sulfate, dextran sulfate, magnesium ion, and polyoxyethylene-polyoxypropylene block copolyether, (ii) an amphoteric surface active agent and aliphatic amines having either of carboxyl group and sulfonate group, and (iii) polycation.

When polycation is used as the reagent, it is preferable to make the polycation react with the sample in the presence of a weak ion exchanger. The weak ion exchanger adsorbs the neutral lipid included in the sample and thus effectively prevents the neutral lipid from being adsorbed on the surface of the electrode and interfering with the electrode reaction.

Typical examples of the amphoteric surface active agent include laurylbetaine, coconut oil fatty acid amidopropylbetaine, amidopropylbetaine laurate, 2-alkyl-N-carboxymethyl-N-hydroxyethylimidazoliniumbetaine, and 2-alkyl-N-carboxyethyl-N-hydroxyethylimidazoliniumbetaine.

Typical examples of the aliphatic amines having either carboxyl group or sulfonate group include alanine, glutamine, glutamic acid, N-(2-acetamido)-2-aminoethanesulfonic acid, N,N-bis(2-hydroxyethyl)-2-aminoethanesulfonic acid, N-cyclohexyl-2-aminoethanesulfonic acid, 2-{4-(2-hydroxyethyl)-1-piperazinyl}ethanesulfonic acid, 2-morpholinoethanesulfonic acid, piperazine-1,4-bis(2-ethanesulfonic acid), N-tris(hydroxymethyl)methyl-2-aminoethanesulfonic acid, N-cyclohexyl-3-aminopropanesulfonic acid, N-cyclohexyl-2-hydroxy-3-aminopropanesulfonic acid, 3-{N,N-bis(2-hydroxyethyl)amino}-2-hydroxypropanesulfonic acid, 3-{4-(2-hydroxyethyl)-1-piperazinyl}propanesulfonic acid, 2-hydroxy-3-{4-(2-hydroxyethyl)-1-piperazinyl}propanesulfonic acid, 3-morpholinopropanesulfonic acid, 2-hydroxy-3-morpholinopropanesulfonic acid, piperazine-1,4-bis(2-hydroxy-3-propanesulfonic acid), N-tris(hydroxymethyl)methyl-3-aminopropanesulfonic acid, 2-hydroxy-N-tris(hydroxymethyl)methyl-3-aminopropanesulfonic acid, N-(2-acetamido)iminodiacetic acid, N,N-bis(2-hydroxyethyl)glycine, and N-{tris(hydroxymethyl)methyl}glycine.

Because of the enhanced regulation of the reactivity, acyl polycations and alkyl polycations are preferably used for the polycation.

In the step (a-1), the lipoproteins other than the low density lipoprotein included in the sample attach to the reagent or reagents to form a water-soluble complex. This lowers the reactivity of the oxidoreductase with cholesterol in the lipoproteins other than the low density lipoprotein. In the subsequent step (b), only cholesterol in the low density lipoprotein is thus involved in the reaction with the oxidoreductase.

The step (a-2) is discussed in detail.

The step (a-2) makes the lipoproteins other than the low density lipoprotein included in the sample adsorbed and/or agglutinated by the reagents for the purpose of removal.

This step uses an antibody against the high density lipoprotein or silica, polyanion, and divalent cation as the reagents. The high density lipoprotein specifically includes apoproteins Apo A-I and Apo A-II, so that the antibody against the high density lipoprotein may be an antibody against Apo A-I or Apo A-II. The antibody against the high density lipoprotein agglutinates the high density lipoprotein included in the sample. The functions of the polyanion and the divalent cation agglutinate the very low density lipoprotein and the chylomicron included in the sample. This process accordingly separates and removes the high density lipoprotein, the very low density lipoprotein, and the chylomicron from the sample.

Silica used as the reagent adsorbs the high density lipoprotein included in the sample for separation and removal thereof.

In the step (a-2), filtration means, such as a filter, is preferably used to separate and remove the agglutinated high density lipoprotein, very low density lipoprotein, and chylomicron from the sample.

Because of no interference with the enzyme reaction, any of dextran sulfate, heparin, phosphotungstic acid, and polyvinyl sulfate is preferably used for the polyanion.

Because of no interference with the enzyme reaction, any of calcium ion, manganese ion, and magnesium ion is preferably used for the divalent cation.

In the step (a-2), the lipoproteins other than the low density lipoprotein included in the sample are adsorbed and/or agglutinated by the reagents and are thereby removed. This process enables only cholesterol in the low density lipoprotein to be involved in the reaction with the enzyme in the subsequent step (b).

The step (b) is discussed in detail.

The step (b) causes only cholesterol included in the low density lipoprotein in the sample to be oxidized by an oxidoreductase, which specifically reacts with cholesterol, and accordingly reduces the electron mediator.

The oxidoreductase and the electron mediator used here may be any known substances conventionally used for the electrochemical determination of cholesterol.

The step (c) is discussed in detail.

The step (c) electrochemically oxidizes the electron mediator, which has been reduced in the step (b), and measures the value of oxidation current. The observed value of oxidation current determines the concentration of cholesterol in the low density lipoprotein.

The technique of the present invention electrochemically determines the concentration of cholesterol and is thus applicable for originally colored samples like blood samples.

Figure 1:
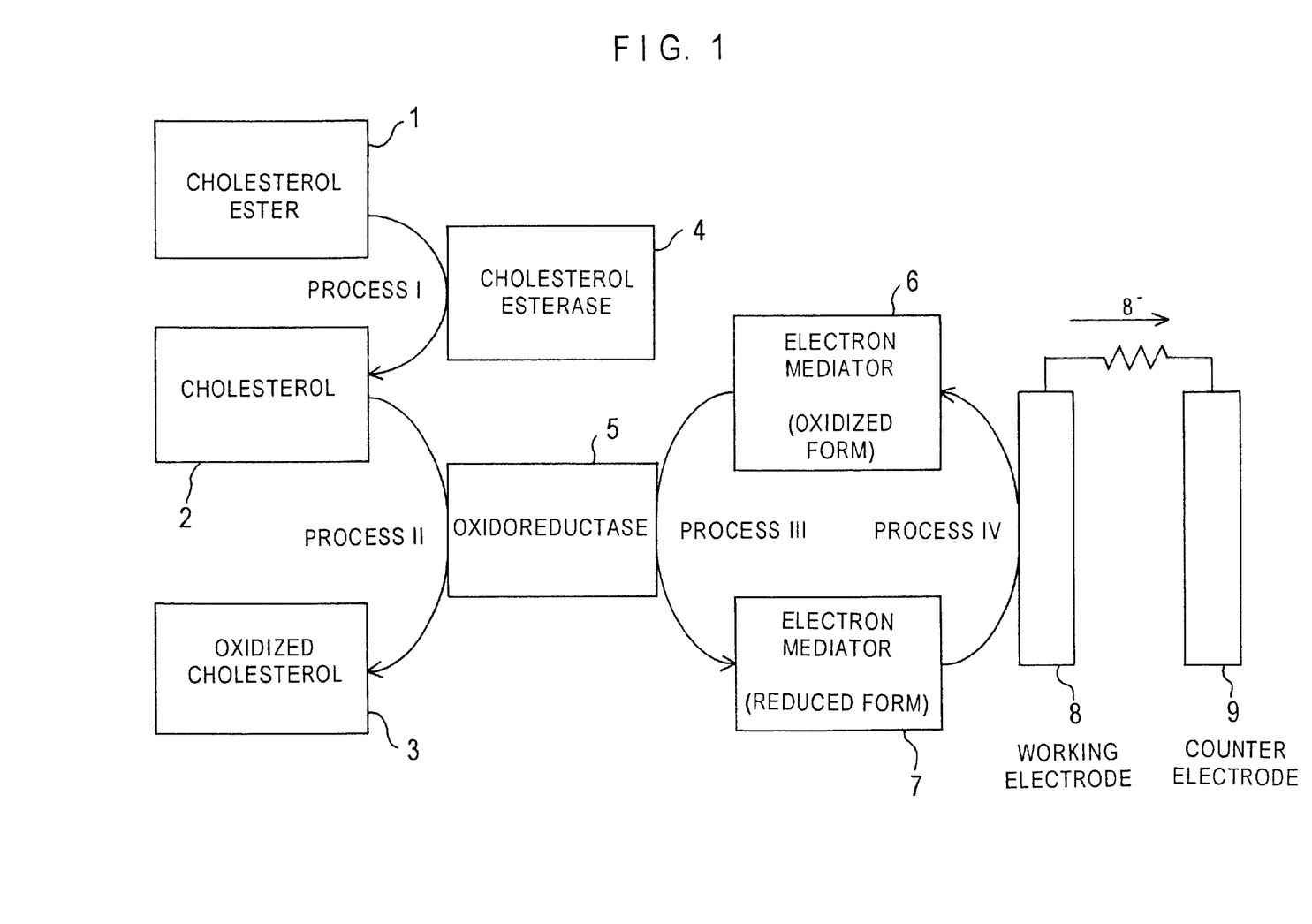
FIG. 1 is a flowchart showing the principle of reactions for determining the concentration of cholesterol according to the present invention.

The principle of the reactions used for determining the concentration of cholesterol according to the present invention are described with referring to FIG. 1.

Cholesterol in lipoproteins included in a sample are mostly bonded to fatty acids via the ester linkage and are present in the form of cholesterol esters. Cholesterol esterase 4 de-esterifies cholesterol ester 1 to give cholesterol 2 (process I).

Oxidoreductase 5 oxidizes cholesterol 2 to yield oxidized cholesterol 3 (process II). This oxidation reaction simultaneously reduces an electron mediator (oxidized form) 6 (process III).

Application of a voltage between a working electrode 8 and a counter electrode 9 to make the working electrode 8 positive causes an electron mediator (reduced form) 7 to be oxidized on the working electrode 8 (process IV). The electric current running in the process of oxidation depends upon the concentration of the electron mediator (reduced form) 7, which is dependent on the concentration of cholesterol 2. Measurement of the electric current running between the working electrode 8 and the counter electrode 9 accordingly determines the concentration of cholesterol 2.

Concrete examples of the sensor and the method of determining cholesterol in the low density lipoprotein are described with reference to the drawings.

EXAMPLE 1

Figure 2:
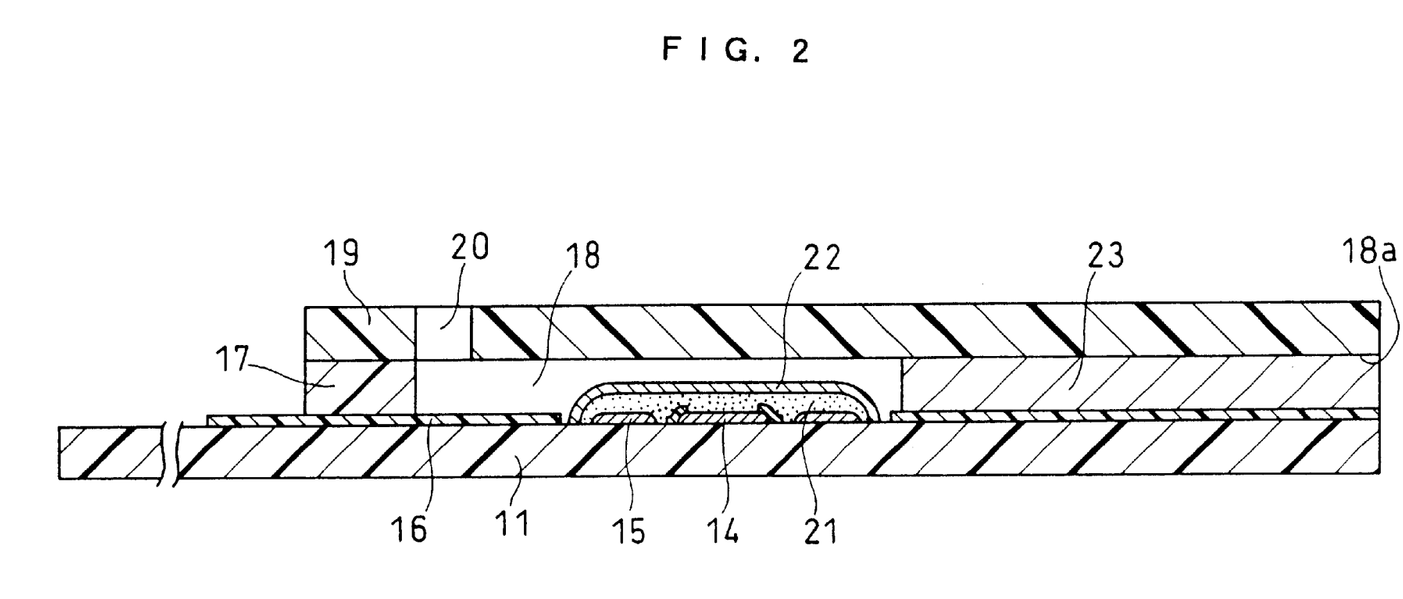
FIG. 2 is a vertical sectional view schematically illustrating the structure of a cholesterol sensor in Example 1 of the present invention.
Figure 3:
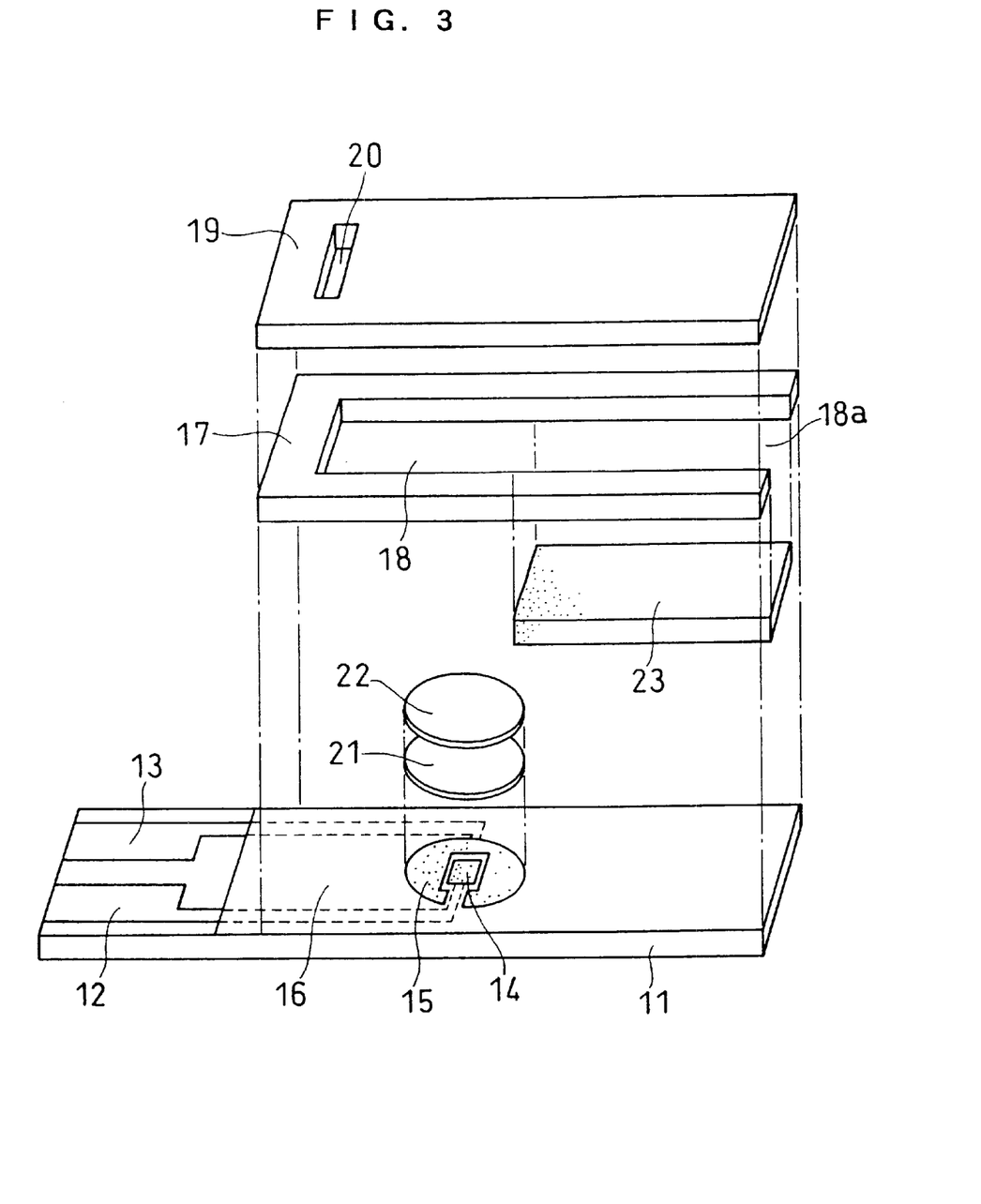
FIG. 3 is a decomposed perspective view showing the cholesterol sensor of Example 1.

FIG. 2 is a sectional view schematically illustrating the structure of a sensor in Example 1 according to the present invention, and FIG. 3 is a decomposed perspective view showing the sensor. The procedure screen prints silver paste on an electrical insulating base plate 11 composed of polyethylene terephthalate, and heats and dries the screen print to form bases of two electrodes and leads 12 and 13 connecting therewith. The procedure then screen prints carbon paste to form a working electrode 14 and a counter electrode 15. A dielectric layer 16 screen printed on the base plate defines the exposed parts of the electrode system.

The procedure subsequently screen prints ink containing sodium salt of carboxymethylcellulose, which is a water-soluble polymer, to cover the electrode system including the working electrode and the counter electrode and dries the screen print at 50° C. for 15 minutes to form a water-soluble polymer layer 21. The procedure then adds an aqueous mixed solution containing cholesterol oxidase, cholesterol esterase, and potassium hexacyanoferrate(III) dropwise to cover the water-soluble polymer layer 21 and dries at 50° C. for 15 minutes to form an enzyme layer 22.

Any of p-benzoquinone and its derivatives, phenazine methosulfate, Methylene Blue, ferrocene and its derivatives may be used for the electron mediator.

The procedure joins a cover 19 having an air vent 20 formed therein with a spacer 17 having a slit 18 formed therein, adds an aqueous mixed solution containing α-cyclodextrin sulfate, dextran sulfate, magnesium Ion, and polyoxyethylene-polyoxypropylene block copolyether dropwise in a recess defined by the slit 18 of the spacer 17, and dries to form a reagent layer 23. The reagent layer 23 Is arranged before the enzyme layer 22 in a sample solution supply path to the electrode system.

The procedure then bonds the base plate 11 with the water-soluble polymer layer 21 and the enzyme layer 22 formed thereon to the cover member Including the cover 19 and the spacer 17 with the reagent layer 23 formed thereon, so as to assemble the biosensor. In this biosensor, the hollow space defined by the slit 18 of the spacer 17 forms the sample solution supply path. An open end 18a of the slit 18 forms an opening of the sample solution supply path or a sample inlet.

When a sample, for example, a blood sample, is brought into contact with the sample inlet, the sample is sucked into the air vent 20 by capillarity of the sample solution supply path.

The procedure may fix a carrier like a glass filter at the position of the reagent layer 23, adds the aqueous solution of the above reagents dropwise in the carrier or on the surface of the carrier, and dries to make the reagents carried on the carrier. Any of filter papers, glass filters, thin layer chromatography carriers, cellulose fibers, fibrous sheets of polymer compounds, papers, and cork may be used for the carrier. Glass filters and cellulose fibers are preferably used since they hardly adsorb the oxidoreductase.

The arrangement of carrying at least one of the electron mediator and the oxidoreductase together with the surface active agent enhances the solubility and thereby desirably shortens the reaction time.

The arrangement of forming at least one of the water-soluble polymer layer, the enzyme layer, and the reagent layer by the freeze drying technique enhances the solubility and thereby desirably shortens the reaction time. Especially when the reagent layer is arranged to partly block the sample solution supply path as in the illustrated example, it is desirable to form a porous reagent layer by the freeze drying technique. The porous reagent layer readily dissolves and absorbs the sample solution, which is in contact with the reagent layer.

The following describes an example of determining the concentration of cholesterol in the low density lipoprotein in a blood sample with the biosensor manufactured in the above manner. The measurement procedure first feeds the blood sample through the sample inlet. The reagent layer that is first in contact with the blood sample, the enzyme layer, and the water-soluble polymer layer are dissolved in this sequence. α-Cyclodextrin sulfate, dextran sulfate, and magnesium ion in the reagent layer cooperatively work to form a water-soluble complex with very low density lipoprotein and chylomicron in the blood sample. Polyoxyethylene-polyoxypropylene block copolyether in the reagent layer works to form a water-soluble complex with high density lipoprotein in the blood sample. This reduces the reactivity of the enzyme with cholesterol in the lipoproteins other than the low density lipoprotein.

The procedure then activates cholesterol esterase and cholesterol oxidase as the enzymes. Only cholesterol in the low density lipoprotein is subject to the catalytic reaction with the enzymes. This enables determination of cholesterol in the low density lipoprotein. Based on the principle of the reactions shown in FIG. 3 ((FIG. 1)), cholesterol esterase in the enzyme layer converts the cholesterol ester in the low density lipoprotein into free cholesterol. The free cholesterol produced by the function of cholesterol esterase and the free cholesterol originally present in the low density lipoprotein are then oxidized by the function of cholesterol oxidase. At the same time, potassium hexacyanoferrate(III) in the enzyme layer is reduced to potassium hexacyanoferrate(II). When a predetermined time elapses after the supply of the blood sample, the procedure applies a voltage of, for example, 500 mV for 5 seconds between the working electrode and the counter electrode to make the working electrode positive, and measures the value of electric current after 5 seconds. This value of electric current is specified as the response value.

The procedure of Example 1 does not determine the concentration of cholesterol based on the degree of color development of a coloring matter and thus enables cholesterol to be determined even in originally colored samples like blood samples. The reagent layer 23 is spatially separated from the enzyme layer 22. The sample fed to the reagent layer 23 first reacts with the reagents in the reagent layer 23 and then reaches the enzyme layer 22 to react with the oxidoreductase and the electron mediator in the enzyme layer 22. This arrangement enables cholesterol in the low density lipoprotein included in the sample to be determined with high reproducibility and high accuracy by only one feed of the sample without requiring the complicated, troublesome operations that separately add the plural reagents to the sample at different timings.

In Example 1, the combination of α-cyclodextrin sulfate, dextran sulfate, magnesium ion, and polyoxyethylene-polyoxypropylene block copolyether is used as the reagent group included in the reagent layer 23. This reagent group may be replaced by another reagent group of an amphoteric surface active agent and aliphatic amines having either carboxyl group or sulfonate group. The reagent group may alternatively be replaced by polycation. In the last case, it is preferable to add a weak ion exchanger to the polycation. Any of acyl and alkyl polycations is preferably used for the polycation. An especially preferable example of the polycation is polyethylene-imine.

A pH buffer may be added to the reagent layer 23. Any of Good's buffers like 3-morpholinopropanesulfonic acid, 2-{4-(2-hydroxyethyl)-1-piperazinyl}ethanesulfonic acid, 2-morpholinoethanesulfonic acid, and piperazine-1,4-bis(2-ethanesulfonic acid) and phosphate buffers may be used for the pH buffer.

EXAMPLE 2

Figure 4:
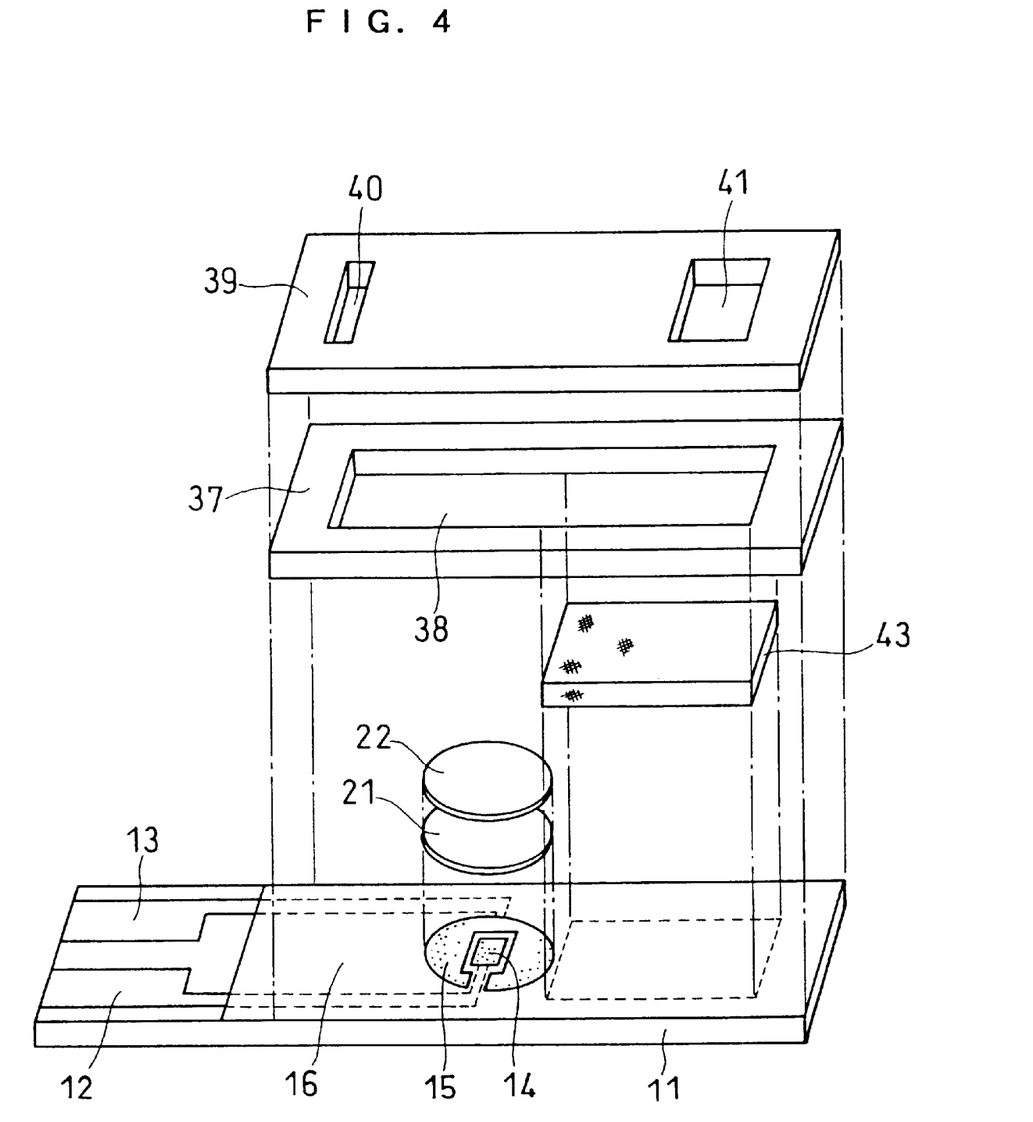
FIG. 4 is a decomposed perspective view showing another cholesterol sensor in Example 2 of the present invention.

FIG. 4 is a decomposed perspective view illustrating a cholesterol sensor in Example 2 according to the present invention. One major difference from Example 1 is that the cholesterol sensor of Example 2 uses a glass filter.

As in the case of Example 1, the water-soluble polymer layer 21 and the enzyme layer 22 are formed on the electrode system of the working electrode 14 and the counter electrode 15 on the base plate 11. The biosensor is completed by combining a spacer 37 having a rectangular through hole 38 formed therein, a cover 39 having an air vent 40 and a sample inlet 41 formed therein, and a filter 43 with the base plate 11.

The filter 43 is arranged before the enzyme layer 22 in the sample solution supply path defined by the through hole 38 of the spacer 37. A sample solution fed through the sample inlet 41 is absorbed by the filter 43 and transmitted through the sample solution supply path to the electrode system by capillarity thereof. The filter 43 is impregnated with an antibody against the high density lipoprotein, dextran sulfate as the polyanion, and calcium ion.

Any of filter papers, cellulose fibers, fibrous sheets of polymer compounds, membrane filters, meshes, and cotton may be used for the filter. The pore diameter of the filter is preferably in the range of 0.05 to 0.5 μm.

The following describes the procedures of determining the concentration of cholesterol in the low density lipoprotein in a blood sample with this biosensor.

The measurement procedure first feeds the blood sample through the sample inlet 41 onto the filter 43. The blood cells in the blood sample are filtered out by the filter 43, and the plasma component goes toward the air vent 40. At the same time, the antibody against the high density lipoprotein in the filter agglutinates the high density lipoprotein in the blood sample. The agglutinated high density lipoprotein is caught on the meshes of the filter and does not reach the enzyme layer 22. The chylomicron and the very low density lipoprotein in the blood sample are agglutinated by dextran sulfate and calcium ion in the filter. The agglutinated lipoprotein is caught on the meshes of the filter and do not reach the enzyme layer. The plasma component reaching the enzyme layer thus includes only the low density lipoprotein among the various lipoproteins.

In the enzyme layer 22, cholesterol esterase and cholesterol oxidase as the enzymes act on the low density lipoprotein, and cholesterol in the low density lipoprotein is subject to the catalytic reaction with the enzymes. In the same manner as Example 1, this determines the concentration of cholesterol in the low density lipoprotein.

The antibody against the high density lipoprotein used as the reagent for agglutinating the high density lipoprotein may be replaced by silica that adsorbs the high density lipoprotein. Silica adsorbs the high density lipoprotein in the sample and thus prevents the high density lipoprotein from reaching the enzyme layer. In this case, the plasma component reaching the enzyme layer also includes only the low density lipoprotein among the various lipoproteins. A pH buffer may further be added to the filter 43.

Like the procedure of Example 1, the procedure of Example 2 does not determine the concentration of cholesterol based on the degree of color development of a coloring matter and thus enables cholesterol to be determined even in originally colored samples like blood samples. The reagents are carried on the filter 43, which is spatially separated from the enzyme layer 22. The sample fed onto the filter first reacts with the reagents in the filter and then reaches the enzyme layer 22 to react with the oxidoreductase and the electron mediator in the enzyme layer 22. This arrangement enables cholesterol in the low density lipoprotein included in the sample to be determined with high reproducibility and high accuracy by only one feed of the sample without requiring the complicated, troublesome operations that separately add the plural reagents to the sample at different timings.

In the illustrated example, the reagents are carried on the filter 43. The reagents may, however, be arranged separately from the filter. In this modified structure, a membrane filter is formed on the enzyme layer 22, and a reagent layer or a carrier with the reagents carried thereon is disposed at the position of the filter 43. When the reagents are separated from the filter, the reagents should be arranged before the filter in the sample solution supply path to the electrode system.

In Example 2, dextran sulfate is used for the polyanion included in the filter 43 as one of the reagent. Dextran sulfate may, however, be replaced with any of heparin, phosphotungstic acid, and polyvinyl sulfate. Calcium ion used for the divalent cation may be replaced with manganese ion or magnesium ion.

In Example 2, the combination of the antibody against the high density lipoprotein, the polyanion, and the divalent cation is used as the reagent group included in the filter 43. This reagent group may be replaced by another reagent group of silica, polyanion, and divalent cation. In the latter case, when the sample is brought into contact with the filter 43, the high density lipoprotein in the sample is adsorbed by silica and does not reach the enzyme layer 22. The very low density lipoprotein and the chylomicron in the sample are agglutinated and filtered out by the filter 43 and thus do not reach the enzyme layer 22 in the same manner as discussed above.

In Examples 1 and 2, the base plate 11 is composed of polyethylene terephthalate. The material of the base plate 11 is, however, not specifically restricted as long as it has electrical insulating properties and some rigidity. For example, the material may be any of thermoplastic resins like polyethylene, polystyrene, polyvinyl chloride, polyamide, and saturated polyester, and thermosetting resins like urea resin, melamine resin, phenol resin, epoxy resin, and unsaturated polyester resin.

In the above examples, the electrodes are formed by screen printing carbon paste on the base plate 11. Another applicable method forms metal electrodes like palladium by vapor deposition or sputtering.

The above examples use cholesterol oxidase and cholesterol esterase for the oxidoreductase and potassium hexacyanoferrate(III) for the electron mediator. Any of other known substances may be used instead. For example, cholesterol dehydrogenase may replace cholesterol oxidase, and p-benzoquinone may be used for the electron mediator.

It is preferable that the enzyme layer 22 includes cholesterol esterase. A surface active reagent may further be added to the enzyme layer 22 to facilitate dissolution of cholesterol in the lipoprotein.

The water-soluble polymer layer is formed over the electrode system for the purpose of protecting the electrodes, though not essential.

A carrier with the reagents carried thereon is preferably used for the reagent layer 23 in Example 1 and in the case of separating the reagents from the filter 43 in Example 2. The presence of the carrier extends the time period for which the sample passes through the reagent layer. The extended time period enables the reaction of the reagents included in the reagent layer with the lipoproteins other than the low density lipoprotein included in the sample to sufficiently proceed until the sample reaches the enzyme layer 22. The carrier is not specifically restricted as long as it can carry the reagents thereon. Typical examples of the carrier include glass filters, filter papers, membrane filters, meshes, and cotton. The reagents carried on the carrier may be in the dried solid state, in the liquid state, or in the gel state.

Industrial Applicability

The technique of the present invention is not the measurement based on the degree of color development of a coloring matter and thus enables cholesterol included in low density lipoprotein to be determined even in colored samples like blood samples. The technique ensures determination of cholesterol included in the low density lipoprotein with high reproducibility and high accuracy by only one feed of the sample. The technique of the present invention does not require any complicated, troublesome operations and is thus suitable for a domestic kit of measuring cholesterol in the low density lipoprotein.

What is claimed is:

1. A cholesterol sensor for determining cholesterol in low density lipoprotein, said cholesterol sensor comprising: an electrically insulating base plate; an electrode system that is mounted on the base plate and includes at least a working electrode and a counter electrode; an enzyme layer formed on the base plate with the electrode system; and a reagent layer that is arranged before the enzyme layer in a sample solution supply path to the electrode system, wherein the enzyme layer comprises at least an oxidoreductase and an electron mediator, and the reagent layer comprises a reagent that attaches to lipoproteins other than the low density lipoprotein to form a water-soluble complex.

2. The cholesterol sensor in accordance with claim 1, wherein the reagent layer comprises α-cyclodextrin sulfate, dextran sulfate, magnesium ion, and polyoxyethylene-polyoxypropylene block copolyether.

3. The cholesterol sensor in accordance with claim 1, wherein the reagent layer comprises an amphoteric surface active agent and aliphatic amines having either of carboxyl group and sulfonate group.

4. The cholesterol sensor in accordance with claim 1, wherein the reagent layer comprises polycation.

5. The cholesterol sensor for determining cholesterol in low density lipoprotein, said cholesterol sensor comprising: an electrically insulating base plate; an electrode system that is mounted on the base plate and includes at least a working electrode and a counter electrode; an enzyme layer formed on the base plate with the electrode system; a filter that is arranged before the enzyme layer in a sample solution supply path to the electrode system; and a reagent layer that is either carried on the filter or arranged before the filter in the sample solution supply path, wherein the enzyme layer comprises at least an oxidoreductase and an electron mediator, and the reagent layer comprises a reagent that functions to adsorb and/or agglutinate lipoproteins other than the low density lipoprotein.

6. The cholesterol sensor In accordance with claim 5, wherein the reagent layer comprises polyanion, divalent cation, and either an antibody against high density lipoprotein or silica.

7. A method of determining cholesterol in low density lipoprotein, said method comprising the steps of:
  (a) causing a sample to react with any reagent or reagent group selected from the group consisting of (i), (ii), and (iii) specified below:
    (i) α-cyclodextrin sulfate, dextran sulfate, magnesium ion, and polyoxyethylene-polyoxypropylene block copolyether.
    (ii) an amphoteric surface active agent and aliphatic amines having either of carboxyl group and sulfonate group, and
    (iii) polycation;
  (b) subsequently causing the sample to react with an oxidoreductase, which specifically reacts with cholesterol, and an electron mediator; and
  (c) electrochemically oxidizing the electron mediator, which has been reduced in said step (b), so as to measure a value of oxidation current.

8. A method of determining cholesterol in low density lipoprotein, said method comprising the steps of:
  (a) causing a sample to react with polyanion, divalent cation, and either an antibody against high density lipoprotein or silica;
  (b) subsequently causing the sample to react with an oxidoreductase, which specifically reacts with cholesterol, and an electron mediator; and
  (c) electrochemically oxidizing the electron mediator, which has been reduced in said step (b), so as to measure a value of oxidation current.

* * * * *